United States Patent [19]
Leppard et al.

[11] Patent Number: 4,465,757
[45] Date of Patent: Aug. 14, 1984

[54] RECORDING MATERIAL FOR COLOR PHOTOGRAPHY

[75] Inventors: David G. Leppard, Marly; Jean Rody, Riehen, both of Switzerland

[73] Assignee: Ciba-Geigy A.G., Basel, Switzerland

[21] Appl. No.: 533,530

[22] Filed: Sep. 16, 1983

[30] Foreign Application Priority Data

Sep. 21, 1982 [CH] Switzerland ............... 5578/82

[51] Int. Cl.$^3$ .................... G03C 5/54; G03C 7/26
[52] U.S. Cl. .................... 430/216; 430/512; 430/523; 430/551; 430/17
[58] Field of Search ........ 430/551, 512, 372, 17, 430/523, 216; 524/99

[56] References Cited

U.S. PATENT DOCUMENTS

| | | | |
|---|---|---|---|
| 2,596,926 | 5/1952 | Gunther et al. | 430/372 |
| 3,183,219 | 5/1965 | Schuler | 430/512 |
| 4,197,236 | 4/1980 | Rosenberger et al. | 524/99 |
| 4,268,593 | 5/1981 | Leppard et al. | 430/551 |

FOREIGN PATENT DOCUMENTS 2126187 12/1971 Fed. Rep. of Germany .
2647452 5/1977 Fed. Rep. of Germany .
1326889 8/1973 United Kingdom .

Primary Examiner—J. Travis Brown
Attorney, Agent, or Firm—Wenderoth, Lind & Ponack

[57] ABSTRACT

Compounds of the formula I

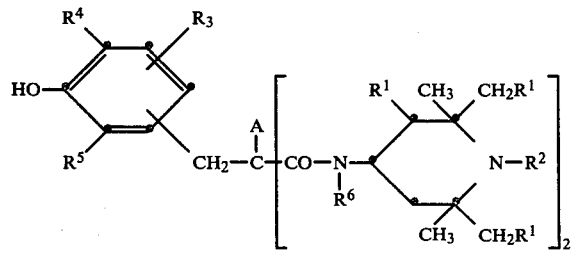

in which A, $R^1$, $R^2$, $R^3$, $R^4$, $R^5$ and $R^6$ are as defined in claim 1, are effective optical stabilizers for photographic dyes and their precursors. They are added to the colorphotographic recording materials as the latter are being prepared, and, as a result, the developed images have a longer optical stability.

5 Claims, No Drawings

RECORDING MATERIAL FOR COLOR PHOTOGRAPHY

The present invention relates to a recording material for colour photography, which contains a specific polyalkylpiperidine compound as a stabiliser in at least one light-sensitive silver halide emulsion layer and/or in at least one of the customary auxiliary layers.

As sterically hindered amines, polyalkylpiperidines are generally known for use as optical stabilisers for organic materials, in particular for polymers. German Offenlegungsschrift No. 2,126,954 already proposes using such polyalkylpiperidines as agents against the fading of colour photographs. European Pat. No. A 11,051 further proposes using, as optical stabilisers for colour photographs, certain polyalkylpiperidine derivatives which contain at least one phenol group. These polyalkylpiperidine derivatives are polyalkylpiperidine esters of hydroxybenzylmalonic acids.

In continuance of this research work, it has been found that amides of phenolalkanecarboxylic acids and 4-aminopolyalkylpiperidines likewise have an excellent optical stabilising action for colour photographs and, moreover, also effect in the dark a stabilisation of the dyes to changes during storage of the recording material.

Accordingly, the present invention relates to a recording material for colour photography which, in at least one light-sensitive silver halide emulsion layer, an intermediate layer, an image-receiving layer and/or a protective layer, contains, as stabiliser, at least one polyalkylpiperidine compound of the formula I

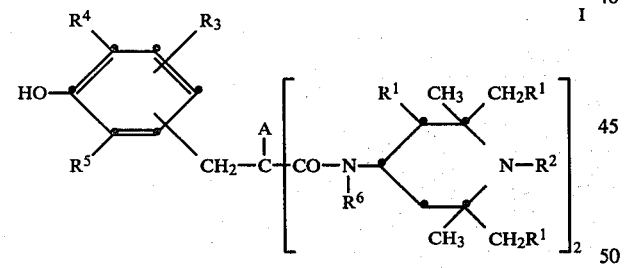

in which $R^1$ is hydrogen or methyl, $R^2$ is hydroxyl, $C_1$–$C_{12}$-alkyl, $C_3$–$C_6$-alkenyl, $C_3$–$C_4$-alkynyl, $C_7$–$C_{12}$-aralkyl, gycidyl, $C_1$–$C_4$-alkyl which is substituted by halogen, cyano, —COOR$^7$ or —CON(R$^8$)(R$^9$), or a —CO—R$^{10}$, —CO—OR$^7$, —CO—N—(R$^8$)(R$^9$), —CH$_2$—CH(R$^{11}$)—OR$^{12}$, —SO—R$^{13}$, —SO$_2$—R$^{13}$, —OR$^7$ or —OOC—R$^{10}$ group, $R^3$ is hydrogen or methyl, $R^4$ is $C_1$–$C_8$-alkyl, $C_5$–$C_8$-cycloalkyl, $C_7$–$C_9$-phenylalkyl, phenyl or $C_7$–$C_{10}$-alkylphenyl, $R^5$ is hydrogen, $C_1$–$C_8$-alkyl, $C_5$–$C_8$-cycloalkyl, $C_7$–$C_9$-phenylalkyl, phenyl or $C_7$–$C_{10}$-alkylphenyl, $R^6$ is hydrogen, $C_1$–$C_{18}$-alkyl, $C_3$–$C_6$-alkenyl, $C_3$–$C_{12}$-cycloalkyl, $C_7$–$C_{12}$-aralkyl, $C_7$–$C_{10}$-alkylphenyl or $C_2$–$C_4$-alkyl which is substituted by —OR$^8$, —N(R$^9$)$_2$ or a group of the formula

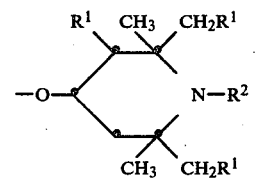

$R^7$ is $C_1$–$C_{12}$-alkyl, allyl, cyclohexyl or benzyl, $R^8$ is $C_1$–$C_{12}$-alkyl, allyl, cyclohexyl, benzyl or phenyl, $R^9$ is hydrogen, $C_1$–$C_{12}$-alkyl, allyl, cyclohexyl or benzyl, or $R^8$ and $R^9$, together with the N atom to which they are bonded, are a 5- or 6-membered heterocyclic ring, $R^{10}$ is hydrogen, $C_1$–$C_{12}$-alkyl, $C_2$–$C_6$-alkenyl, chloromethyl, $C_5$–$C_8$-cycloalkyl, $C_7$–$C_{12}$-aralkyl, phenyl, $C_7$–$C_{10}$-alkylphenyl or phenyl, phenylmethyl or phenylethyl which are substituted by 1 or 2 $C_1$–$C_4$-alkyl groups and a hydroxyl group, $R^{11}$ is hydrogen, $C_1$–$C_4$-alkyl, $C_2$–$C_{13}$-alkoxymethyl, phenyl or phenoxymethyl, $R^{12}$ is hydrogen, $C_1$–$C_{12}$-alkyl, —CO—R$^{10}$ or —CO—N(R$^8$)(R$^9$), $R^{13}$ is $C_1$–$C_{12}$-alkyl, phenyl or $C_7$–$C_{18}$-alkylaryl, A is hydrogen, $C_1$–$C_{18}$-alkyl, $C_1$–$C_{10}$-alkyl which is substituted by at least one of the —OR$^{14}$, —SR$^{15}$, —CN, —CO—X—R$^{16}$, —O—CO—R$^{17}$ or —P(O)(OR$^{18}$)$_2$ groups, $C_2$–$C_{20}$-alkyl which is interrupted by —O—, —S—, —SO— or —SO$_2$—, $C_3$–$C_{18}$-alkenyl, $C_3$–$C_8$-alkenyl, $C_3$–$C_{12}$-cycloalkyl, $C_6$–$C_{10}$-alkylcycloalkyl, $C_6$–$C_{10}$-cycloalkylalkyl, $C_7$–$C_{12}$-aralkyl, $C_8$–$C_{16}$-alkylaralkyl, phenyl, a —CN, —CO— R$^{20}$, —CO$_2$—R$^{21}$ or —P(O)(OR$^{18}$) group or one of the following groups

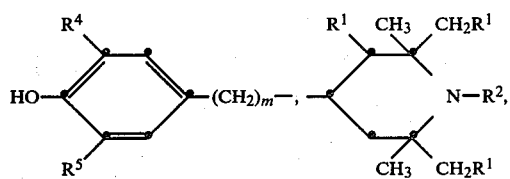

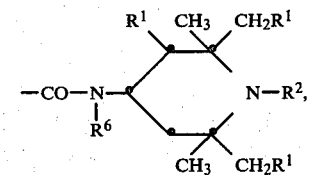

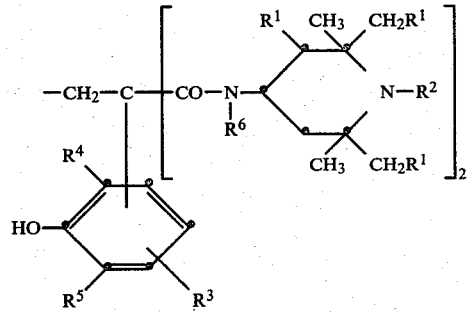

in which X is —O— or —N(R$^{19}$)—, $R^{14}$ is phenyl, benzyl or cyclohexyl, $R^{15}$ is phenyl or $C_7$–$C_9$-phenylalkyl, $R^{16}$ is $C_1$–$C_{18}$-alkyl, $C_5$–$C_8$-cycloalkyl and $R^{17}$ is $C_1$–$C_{18}$-alkyl, $C_5$–$C_8$-cycloalkyl, phenyl, $C_7$–$C_9$-phenylalkyl or a group of the formula

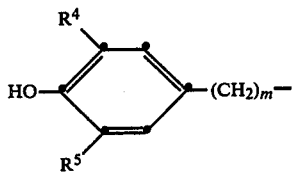

$R^{18}$ is $C_1$–$C_8$-alkyl, allyl or phenyl, $R^{19}$ is hydrogen, $C_1$–$C_{18}$-alkyl, allyl, cyclohexyl, benzyl or phenyl or, together with $R^{16}$ and the N atom, a 5- or 6-membered heterocyclic ring, $R^{20}$ is hydrogen, $C_1$–$C_{18}$-alkyl, $C_2$–$C_6$-alkenyl, $C_5$–$C_8$-cycloalkyl, phenyl, $C_7$–$C_{10}$-alkylphenyl or $C_7$–$C_9$-phenylalkyl, $R^{12}$ is $C_1$–$C_{18}$-alkyl, cyclohexyl, phenyl, naphthyl, $C_7$–$C_{18}$-alkylaryl, $C_7$–$C_9$-phenylalkyl or a group of the formula

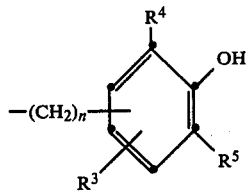

m is zero, 1 or 2, and n is zero, 1, 2 or 3.

In the formula I, $R^4$, $R^5$ and $R^{18}$ can be $C_1$–$C_8$-alkyl, and as such they can be unbranched or branched alkyl, for example, methyl, ethyl, propyl, isopropyl, butyl, tert.-butyl, isoamyl, n-hexyl, 2-ethylbutyl, n-octyl or 1,1,3,3-tetramethylbutyl. $C_1$–$C_{12}$-alkyl radicals $R^2$, $R^7$, $R^8$, $R^9$, $R^{10}$, $R^{12}$ and $R^{13}$ can also be for example nonyl, decyl or dodecyl. $C_1$–$C_{18}$-alkyl radicals $R^6$, $R^{16}$, $R^{17}$, $R^{19}$, $R^{20}$, $R^{21}$ and A can moreover also be, for example, tetradecyl, hexadecyl or octadecyl.

$C_3$–$C_6$-alkenyl radicals $R^2$ and $R^6$ can be, for example, allyl, methallyl, 3,3-dimethylallyl or 2-butenyl. $C_2$–$C_6$-alkenyl radicals $R^{10}$ and $R^{20}$ can also be vinyl or isopropenyl. A $C_3$–$C_{18}$-alkenyl radical A can be defined in the same way as $R^2$ and, moreover, be, for example, 2-octenyl, 11-undecenyl or oleyl.

A $C_3$–$C_4$-alkynyl radical $R^2$ can be, for example, 2-propinyl or butinyl. A $C_3$–$C_8$-alkynyl radical A can moreover also be, for example, 2-hexynyl or 2-octynyl.

$C_5$–$C_8$-cycloalkyl radicals $R^4$, $R^5$, $R^{10}$, $R^{16}$, $R^{17}$ and $R^{20}$ can be, for example, cyclopentyl, cyclohexyl or cyclooctyl. $C_3$–$C_{12}$-cycloalkyl radicals $R^6$ and A can moreover also be cyclopropyl, cyclobutyl, cyclodecyl or cyclododecyl.

A $C_6$–$C_{10}$-alkylcycloalkyl radical A can be, for example, methylcyclopentyl, monomethylcyclohexyl, dimethylcyclohexyl, monomethylcyclooctyl or dimethylcyclooctyl. A $C_6$–$C_{10}$-cycloalkylalkyl radical A can be, for example, cyclopentylmethyl, cyclohexylmethyl, cyclohexylethyl or cyclooctylmethyl.

$C_7$–$C_9$-phenylalkyl radicals $R^4$, $R^5$, $R^{15}$, $R^{17}$, $R^{20}$ and $R^{21}$ can be, for example, benzyl, 2-phenylethyl, 3-phenylpropyl or α,α-dimethylbenzyl. $C_7$–$C_{12}$-aralkyl radicals $R^2$, $R^6$, $R^{10}$ and A can moreover also be, for example, phenylbutyl or naphthylmethyl. An alkylaralkyl radical A can be, for example, 4-methylbenzyl, 3-tert.-butylbenzyl, 4-methylnaphthyl-1-methylpropyl or 2-(4-isopropylphenyl)-propyl.

$C_7$–$C_{10}$-alkylphenyl radicals $R^4$, $R^5$, $R^6$, $R^{10}$ and $R^{20}$ can be, for example, 4-methylphenyl, 4-tert.-butylphenyl, 3-isopropylphenyl or 3,5-dimethylphenyl. $C_7$–$C_{18}$-alkylaryl radicals $R^{13}$ and $R^{21}$ can moreover also be, for example, 4-octylphenyl, 4-dodecylphenyl or 4-methylnaphth-1-yl.

$R^8$ and $R^9$ as well as $R^{19}$ and $R^{16}$, in each case together with the N atom to which they are bonded, can be a heterocyclic ring, for example a pyrrolidine, piperidine or morpholine ring.

A can be substituted or interrupted alkyl, for example 2-cyanoethyl, 2-ethoxycarbonylethyl, N-butyl-2-carbamoylethyl, 2-methoxyethyl, 2-phenoxypropyl, 3-phenylthiopropyl, 2-dodecylthioethyl, 2-butylsulfonylethyl, 2-isopropoxypropyl, 2-acetoxybutyl, 2-benzoyloxyethyl or 2-(diethylphosphono)-ethyl.

A $C_2$–$C_{13}$-alkoxymethyl radical $R^{11}$ can be, for example, methoxymethyl, ethoxymethyl, isopropoxymethyl, butoxymethyl, 2-ethylbutoxymethyl, octyloxymethyl or dodecyloxymethyl.

In the phenolic radical of the formula I, the hydroxyl group can be meta or para to the $CH_2$ group, but it preferably is in para position. If the $CH_2$ group is para to the hydroxyl group, $R^3$ is in the meta position. If the $CH_2$ group is in the meta position, $R^3$ is para to the hydroxyl group.

Preferred stabilisers are compounds of the formula II

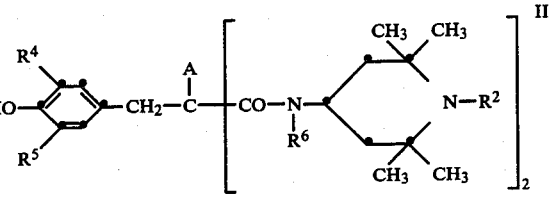

in which $R^2$ is hydroxyl, $C_1$–$C_4$-alkyl, $C_3$–$C_4$-alkenyl, propargyl, benzyl, glycidyl, $C_1$–$C_4$-alkyl which is substituted by halogen, cyano, —$COOR^7$ or —$CON(R^8)(R^9)$, or a —$CO$—$R^{10}$, —$CO$—$OR^7$, —$CO$—$N(R^8)(R^9)$, —$CH_2$—$CH(R^{11})$—$OR^{12}$, —$SO$—$R^{13}$, —$SO_2$—$R^{13}$, —$OR^7$ or —$OOC$—$R^{10}$ group, $R^4$ is $C_1$–$C_4$-alkyl, $R^5$ is hydrogen or $C_1$–$C_4$-alkyl, $R^6$ is hydrogen, $C_1$–$C_{12}$-alkyl, $C_3$–$C_7$-alkoxyalkyl, cyclohexyl or a group of the formula

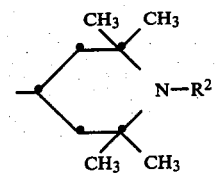

$R^7$ is $C_1$–$C_8$-alkyl, benzyl or cyclohexyl, $R^8$ is $C_1$–$C_8$-alkyl, cyclohexyl or phenyl, $R^9$ is hydrogen or $C_1$–$C_8$-alkyl, or $R^8$ and $R^9$, together with the N atom, are a piperidine or morpholine ring, $R^{10}$ is $C_1$–$C_4$-alkyl, $C_2$–$C_3$-alkenyl, chloromethyl, phenyl, benzyl or a group of the formula

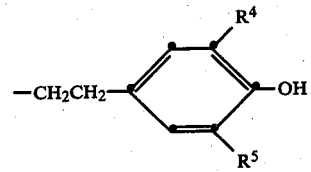

$R^{11}$ is hydrogen, methyl or phenyl, $R^{12}$ is hydrogen, $C_1$-$C_8$-alkyl, —CO—$R^{10}$ or —CO—N($R^8$)($R^9$), $R^{13}$ is $C_1$-$C_4$-alkyl, phenyl or p-tolyl, and A is hydrogen, $C_1$-$C_8$-alkyl, cyano, allyl or benzyl.

Particularly preferred stabilisers are compounds of the formula II in which $R^2$ is hydroxyl, methyl, allyl, benzyl, 2-hydroxyethyl, acetyl, acryloyl, methoxy, acetoxy or a —CO—N($R^8$)($R^9$) group, $R^4$ is tert.-butyl, $R^5$ is methyl or tert.-butyl, $R^6$ is hydrogen or $C_1$-$C_8$-alkyl, $R^8$ is $C_1$-$C_8$-alkyl, phenyl or cyclohexyl, $R^9$ is hydrogen or $C_1$-$8_8$-alkyl, and A is hydrogen, $C_1$-$C_8$-alkyl or benzyl.

Some of the compounds of the formula I described herein are known from German Offenlegungsschrift No. 2,647,452, where the compounds are described as optical stabilisers for plastics and where, moreover, various processes are described for preparing these compounds. To the extent that these compounds are new, they can be prepared analogously to the described compounds.

The synthesis of the compounds preferably starts from N,N'-bis-(polyalkylpiperid-4-yl)-malonamides of the formula III, which are reacted with a mole of alkali and a mole of a halogen compound, A—Hal, to give compounds of the formula IV:

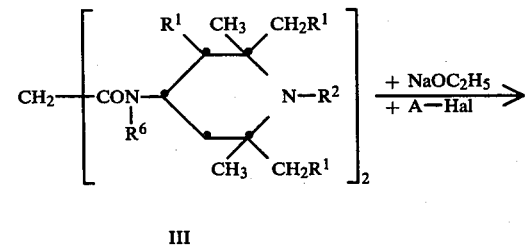

III

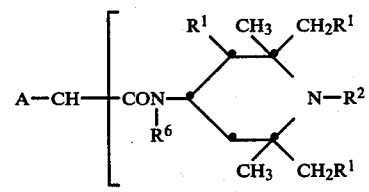

IV

The phenolic radical can be introduced into the amides IV by reaction with the corresponding hydroxybenzyl thiocarbamates, hydroxybenzylamines or hydroxybenzyl alkoxides V:

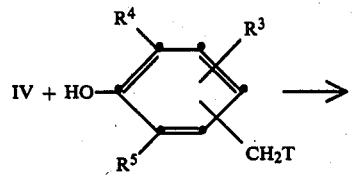

$T = $ —S—CS—$NR_2$ or —$NR_2$ or —OR, $R = C_1$-$C_4$—alkyl.

Alternatively, a compound of the formula III can be reacted with a mole of V, and the radical A can be introduced as the second step.

The order of the reaction steps can be altered as desired, and, for example, a dialkyl malonate can be reacted with A—Hal to give the intermediate A—CH(COOR)$_2$, which is then reacted either first with a compound of the formula V and then with a 4-aminopiperidine compound of the formula VI

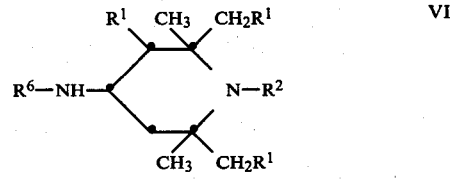

or vice versa.

The 4-aminopiperidines of the formula VI are known from German Offenlegungsschriften Nos. 2,040,975 and 2,349,962, and are prepared by reductive amination of the 4-oxopiperidines.

The radical $R^2$ can be introduced at as early a stage as the synthesis of VI, or after any one of the subsequent synthesis steps.

It can be introduced by the customary methods of N-substituting secondary amines, for example by reaction with the corresponding halogeno compounds Hal—$R^2$.

If $R^2$ is a —$CH_2$—CH($R^{11}$)—$OR^{12}$ radical, it can be introduced by reacting it with an oxirane,

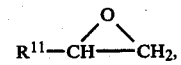

and if desired subsequently alkylating or acylating the hydroxyl group. An $R^2$ hydroxyl group can be introduced by reducing the corresponding N-oxyls. Etherification or esterification of the N-hydroxyl compounds gives the compounds in which $R^2$ is an —$OR^7$ or —OOC—$R^{10}$ group.

Examples of individual compounds of the formula I of the type which, according to the invention, can be used as optical stabilisers for colour photographic recording material are the following compounds:

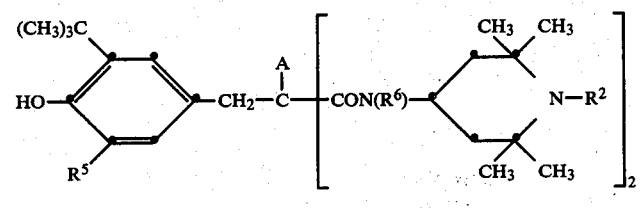

Com-

-continued

| Compound No. | $R^5$ | A | $R^6$ | $R^2$ |
|---|---|---|---|---|
| 1 | —$CH_3$ | H | n-$C_8H_{17}$ | —CO—CH=$CH_2$ |
| 2 | —$CH_3$ | H | n-$C_4H_9$ | —$CH_3$ |
| 3 | —$CH_3$ | H | H | —$CH_3$ |
| 4 | —$CH_3$ | H | —$C_2H_5$ | —CO—$CH_3$ |
| 5 | tert.-butyl | H | H | —CO—CH=$CH_2$ |
| 6 | tert.-butyl | n-$C_4H_9$ | H | —CO—CH=$CH_2$ |
| 7 | tert.-butyl | H | n-$C_4H_9$ | —CO—$CH_3$ |
| 8 | tert.-butyl | —$C_2H_5$ | H | —CO—CH=$CH_2$ |
| 9 | tert.-butyl | n-$C_4H_9$ | H | —$CH_3$ |
| 10 | tert.-butyl | —$C_2H_5$ | H | —$CH_2CH=CH_2$ |
| 11 | tert.-butyl | H | n-$C_4H_9$ | —$CH_3$ |
| 12 | tert.-butyl | H | H | —CO—$CH_3$ |
| 13 | tert.-butyl | H | n-$C_4H_9$ | benzyl |
| 14 | tert.-butyl | —$CH_2CH=CH_2$ | H | —$CH_2CH=CH_2$ |
| 15 | tert.-butyl | H | n-$C_4H_9$ | —CO—CH=$CH_2$ |
| 16 | tert.-butyl | benzyl | H | benzyl |
| 17 | tert.-butyl | benzyl | —$CH_2CH_2OH$ | —$CH_3$ |
| 18 | tert.-butyl | n-$C_4H_9$ | n-$C_4H_9$ | —CO—CH=$CH_2$ |
| 19 | tert.-butyl | n-$C_4H_9$ | n-$C_4H_9$ | benzyl |
| 20 | tert.-butyl | —$C_2H_5$ | n-$C_6H_{13}$ | —$CH_2CH=CH_2$ |
| 21 | tert.-butyl | n-$C_8H_{17}$ | —$CH_3$ | —CO—N($CH_3)_2$ |
| 22 | tert.-butyl | H | cyclohexyl | —$CH_2CH_2OH$ |
| 23 | tert.-butyl | H | 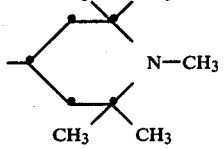 | —CO—$CH_3$ |

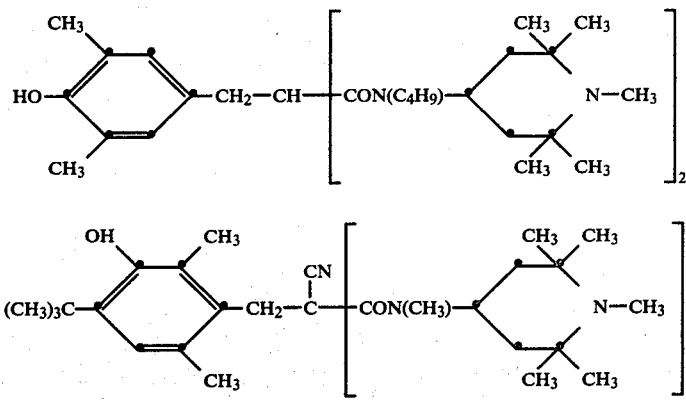

The compounds of the formula I are sparingly soluble in water, and they are therefore preferably added to the photographic layers in the form of a dispersion or emulsion. The stabilisers are generally incorporated into the photographic material together with the colour couplers. For this purpose, the compounds of the formula I are dissolved together with the colour couplers and if desired with further optical stabilisers in a low-boiling organic solvent, such as methyl acetate, ethyl acetate, carbon tetrachloride, chloroform, methanol, ethanol, n-butanol, dioxane, acetone or benzene, a high-boiling organic solvent, such as tricresyl phosphate, N,N-diethyllauramide, di-n-butyl phthalate or ethyl N-diphenylcarbamate, or a solvent mixture of the above-mentioned low-boiling and high-boiling organic solvents, the solution obtained is added to a protective colloid solution, such as, in particular, an aqueous gelatin solution, and the solution is dispersed therein by means of a colloid mill or a homogeniser or by using ultrasound.

The dispersions thus obtained are then used for preparing the layers of recording materials for colour photography. These layers can be, for example, intermediate or protective layers, but in particular light-sensitive (blue-, green- and red-sensitive) silver halide emulsion layers in which the bluish green (cyan), purple (magenta) and yellow dyes are formed from the corresponding colour couplers as the exposed recording material is developed.

If desired, the optical stabiliser can also be applied in the treatment baths which are used after the color-developing, for example in fixing and/or washing baths, but it is necessary for the compounds of the formula I to have a certain solubility in alcohols (methanol/ethanol), aqueous alkali and/or water. If the diffusion transfer method is used, the stabiliser can also be incorporated into a receiving layer.

The silver halide layers can contain any colour couplers, in particular bluish green, purple and yellow couplers, which are used to form said dyes and hence the colour images.

In the photographic recording material according to the present invention, the stabilisers of the formula I can be combined in the same layer not only with the colour couplers but in addition also with ultraviolet absorbers or other optical stabilisers.

The silver halide emulsions preferably contain, as a binder, gelatin, if desired in a mixture with other high molecular weight natural or synthetic compounds.

The silver halide emulsions can be, for example, silver bromide, silver chloride or silver iodide emulsions or even emulsions which contain a mixture of silver halides, for example silver bromide iodide or silver chloride bromide emulsions.

The emulsions can be chemically sensitised, and they can also contain customary organic stabilisers and antifogging agents and also customary plasticisers, for example glycerol. The emulsions can also be hardened by means of the hardening agents customary for gelatin. The emulsions can also contain customary casting aids. The emulsions can be applied to supports customary for photographic recording material.

It is possible to use customary developer baths to develop the colour photographic recording material. These baths generally contain a developer substance of the p-phenylenediamine type, a developing retarder, such as potassium bromide, an antioxidant, such as sodium sulfite or hydroxylamine, and a base, for example an alkali metal hydroxide or alkali metal carbonate. The developing baths can also contain customary antifogging agents and complexing agents.

The optical stabilisers to be used according to the invention are, in certain cases, also suitable for protecting colour photographic layers in which the dyes are incorporated directly into the emulsion and the image is generally by selective bleaching.

The amount of the optical stabiliser(s) can vary within wide limits and is approximately within the range from 1 to 2,000 mg, preferably 100 to 800 and in particular 200–500, mg per m² of the layer into which it (or they) is (or are) incorporated.

If the photographic material contains an agent which absorbs UV radiation, this agent can be present together with the optical stabiliser in one layer or in an adjacent layer. The weight ratio between the ultraviolet absorber and the optical stabiliser of the formula I is about (2–10):1, the molar ratio being about (5–20):1. Examples of ultraviolet absorbers are compounds of the benzophenone, acrylonitrile, thiazolidone, benzotriazole, oxazole, thiazole and imidazole The colour images obtained by exposing and developing the recording material according to the invention have very good light fastness to visible and ultraviolet light. The compounds of the formula I are virtually colourless, so that the images are not discoloured; they are also highly compatible with the customary photographic additives present in the individual layers. Owing to their high effectiveness, it is possible to reduce their level and thus to avoid their precipitating or crystallising when they are incorporated in the form of an organic solution into the aqueous binder emulsions which are used for preparing photographic layers. The optical stabilisers have no adverse effect on the individual processing steps necessary for producing the colour images after the photographic recording material has been exposed. Furthermore the phenomenon of pressure fogging, which can frequently arise in the case of blue-sensitive emulsions, can be largely suppressed. Pressure fogging can arise, for example, when photographic materials (silver halide emulsion layers which are present on a support made of natural or synthetic materials) are subjected to mechanical stresses, for example twisting, bending or rubbing, in the course of their preparation or in the course of the treatment before the developing (T. H. James, The Theory of Photographic Process 4th Edition, Macmillan, New York, N.Y. 1977, page 23 et seq., page 166 et seq.).

The following example illustrates the present invention in more detail without limiting it.

EXAMPLE 0.087 g of the yellow coupler of the formula

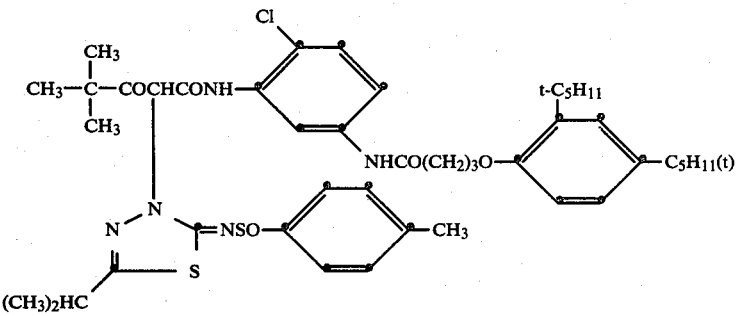

and 0.026 g of one of the optical stabilisers given in the following tables are dissolved in 2.0 ml of a mixture of tricresyl phosphate/ethyl acetate (1.5 g in 100 ml). 7.0 ml of a 6% gelatin solution, 0.5 ml of an 8% solution of the wetting agent of the formula

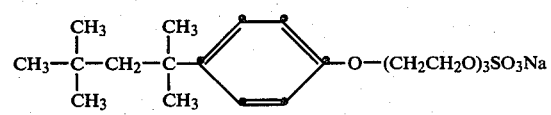

in isopropanol/water (3:4), and 0.5 ml of water are added to this solution and are emulsified therein using 100-Watt ultrasound for 5 minutes. 2.5 ml of the emulsion thus obtained are admixed with 2.0 ml of a silver bromide emulsion with a silver content of 6.0 g per liter, 0.7 ml of a 1% aqueous solution of hardening agent of the formula

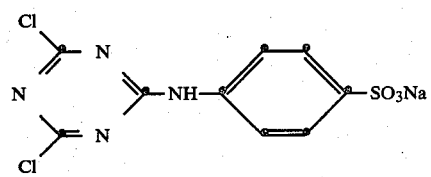

and 3.8 ml of water, and the mixture is brought to pH 6.5 and is cast onto white subbed plastic-coated paper stretched over a glass plate.

When the cast material has solidified, it is dried in a drying cabinet at room temperature by means of circulating air.

7 days later, samples cut to a size of 35×180 mm are exposed under a step wedge with 3,000 Lux.s and are then processed in Kodak's Ektaprint $2^R$ process.

The yellow wedges thus obtained are irradiated in an Atlas Weather-Ometer by means of a 2,500-W xenon lamp to a total of 42 kJoule/cm² (a comparative sample contains no optical stabiliser).

The table shows the percentage decreases in colour density from an original density of 1.0.

| Optical stabiliser No. | Colour density Loss in % (reflectance) |
|---|---|
|  | 49 |
| 1 | 26 |
| 2 | 32 |
| 5 | 30 |
| 7 | 32 |
| 10 | 30 |
| 11 | 30 |

What is claimed is:

1. A recording material for colour photography which, in at least one light-sensitive silver halide emulsion layer, an intermediate layer, an image-receiving layer and/or a protective layer, contains, as a stabiliser, at least one polyalkylpiperidine compound of the formula I

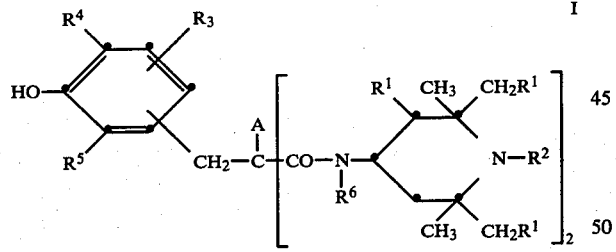

in which $R^1$ is hydrogen or methyl, $R^2$ is hydroxyl, $C_1-C_{12}$-alkyl, $C_3-C_6$-alkenyl, $C_3-C_4$-alkynyl, $C_7-C_{12}$-aralkyl, gycidyl, $C_1-C_4$-alkyl which is substituted by halogen, cyano, —COOR$^7$ or —CON(R$^8$)(R$^9$), or a —CO—R$^{10}$, —CO—OR$^7$, —CO—N—(R$^8$)(R$^9$), —CH$_2$—CH(R$^{11}$)—OR$^{12}$, —SO—R$^{13}$, —SO$_2$—R$^{13}$, —OR$^7$ or —OOC—R$^{10}$ group, $R^3$ is hydrogen or methyl, $R^4$ is $C_1-C_8$-alkyl, $C_5-C_8$-cycloalkyl, $C_7-C^9$-phenylalkyl, phenyl or $C_7-C_{10}$-alkylphenyl, $R^5$ is hydrogen, $C_1-C_8$-alkyl, $C_5-C_8$-cycloalkyl, $C_7-C_9$-phenylalkyl, phenyl or $C_7-C_{10}$-alkylphenyl, $R^6$ is hydrogen, $C_1-C_{18}$-alkyl, $C_3-C_6$-alkenyl, $C_3-C_{12}$-cycloalkyl, $C_7-C_{12}$-aralkyl, $C_7-C_{10}$-alkylphenyl or $C_2-C_4$ alkyl which is substituted by —OR$^8$, —N(R$^9$)$_2$ or a group of the formula

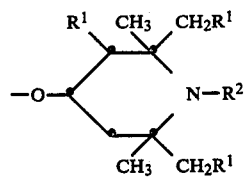

$R^7$ is $C_1-C_{12}$-alkyl, allyl, cyclohexyl or benzyl, $R^8$ is $C_1-C_{12}$-alkyl, allkyl, cyclohexyl, benzyl or phenyl, $R^9$ is hydrogen, $C_1-C_{12}$-alkyl, allyl, cyclohexyl or benzyl, or $R^8$ and $R^9$, together with the N atom to which they are bonded, are a 5-or 6-membered heterocyclic ring, $R^{10}$ is hydrogen, $C_1-C_{12}$-alkyl, $C_2-C_6$-alkenyl, chloromethyl, $C_5-C_8$-cycloalkyl, $C_7-C_{12}$-aralkyl, phenyl, $C_7-C_{10}$-alkylphenyl or phenyl, phenylmethyl or phenylethyl which are substituted by 1 or 2 $C_1-C_4$-alkyl groups and a hydroxyl group, $R^{11}$ is hydrogen, $C_1-C_4$-alkyl, $C_2-C_{13}$-alkoxymethyl, phenyl or phenoxymethyl, $R^{12}$ is hydrogen, $C_1-C_{12}$-alkyl, —CO—R$^{10}$ or —CO—N(R$^8$)(R$^9$), $R^{13}$ is $C_1-C_{12}$-alkyl, phenyl or $C_7-C_{18}$-alkylaryl, A is hydrogen, $C_1-C_{18}$-alkyl, $C_1-C_{10}$-alkyl which is substituted by at least one of the —OR$^{14}$, —SR$^{15}$, —CN, —CO—X—R$^{16}$, —O—CO—R$^{17}$ or —P(O)(OR$^{18}$)$_2$ groups, $C_2-C_{20}$-alkyl which is interrupted by —O—, —S—, —SO— or —SO$_2$—, $C_3-C_{18}$-alkenyl, $C_3-C_8$-alkynyl, $C_3-C_{12}$-cycloalkyl, $C_6-C_{10}$-alkylcycloalkyl, $C_6-C_{10}$-cycloalkylalkyl, $C_7-C_{12}$-aralkyl, $C_8-C_{16}$-alkylaralkyl, phenyl, a —CN, —CO—R$^{20}$, —SO$_2$R$^{21}$ or —P(O)(OR$^{18}$) group or one of the following groups.

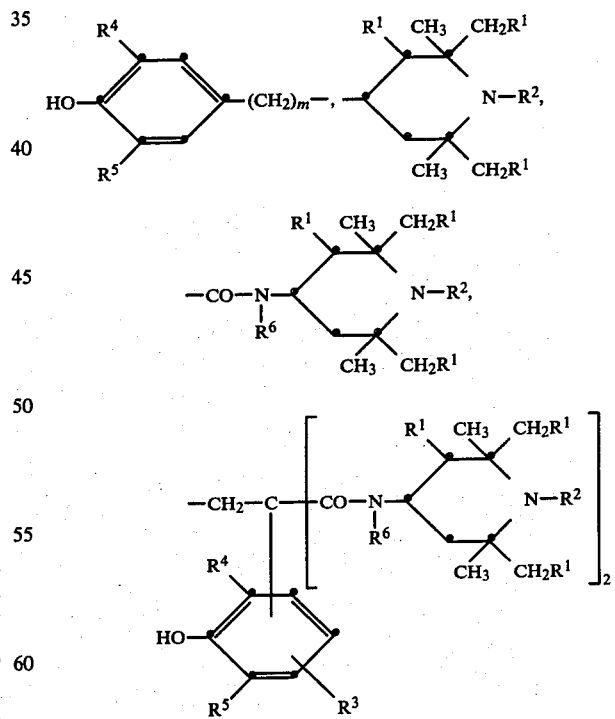

in which X is —O— or —N(R$^{19}$)—, $R^{14}$ is phenyl, benzyl or cyclohexyl, $R^{15}$ is phenyl or $C_7-C_9$-phenylalkyl, $R^{16}$ is $C_1-C_{18}$-alkyl, $C_5-C_8$-cycloalkyl and $R^{17}$ is $C_1-C_{18}$-alkyl, $C_5-C_8$-cycloalkyl, phenyl, $C_7-C_9$-phenylalkyl or a group of the formula

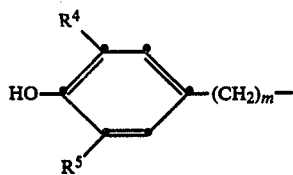

$R^{18}$ is $C_1$–$C_8$-alkyl, allyl or phenyl, $R^{19}$ is hydrogen, $C_1$–$C_{18}$-alkyl, allkyl, cyclohexyl, benzyl or phenyl or, together with $R^{16}$ and the N atom, a 5- or 6-membered heterocyclic ring, $R^{20}$ is hydrogen, $C_1$–$C_{18}$-alkyl, $C_2$–$C_6$-alkenyl, $C_5$–$C_8$-cycloalkyl, phenyl, $C_7$–$C_{10}$-alkylphenyl or $C_7$–$C_9$-phenylalkyl, $R^{21}$ is $C_1$–$C_{18}$-alkyl, cyclohexyl, phenyl, naphthyl, $C_7$–$C_{18}$-alkylaryl, $C_7$–$C_9$-phenylalkyl or a group of the formula

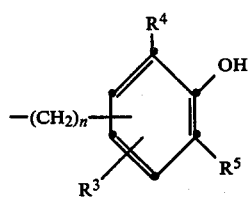

m is zero, 1 or 2, and n is zero, 1, 2 or 3.

2. A recording material for colour photography according to claim 1, wherein the stabiliser is a compound of the formula II

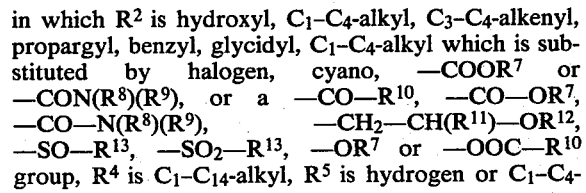

in which $R^2$ is hydroxyl, $C_1$–$C_4$-alkyl, $C_3$–$C_4$-alkenyl, propargyl, benzyl, glycidyl, $C_1$–$C_4$-alkyl which is substituted by halogen, cyano, —COOR$^7$ or —CON(R$^8$)(R$^9$), or a —CO—R$^{10}$, —CO—OR$^7$, —CO—N(R$^8$)(R$^9$), —CH$_2$—CH(R$^{11}$)—OR$^{12}$, —SO—R$^{13}$, —SO$_2$—R$^{13}$, —OR$^7$ or —OOC—R$^{10}$ group, $R^4$ is $C_1$–$C_{14}$-alkyl, $R^5$ is hydrogen or $C_1$–$C_4$-alkyl, $R^6$ is hydrogen, $C_1$–$C_{12}$-alkyl, $C_3$–$C_7$-alkoxyalkyl, cyclohexyl or a group of the formula

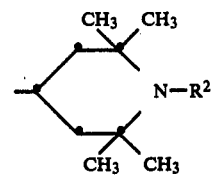

$R^7$ is $C_1$–$C_8$-alkyl, benzyl or cyclohexyl, $R^8$ is $C_1$–$C_8$-alkyl, cyclohexyl or phenyl, $R^9$ is hydrogen or $C_1$–$C_8$alkyl, or $R^8$ and $R^9$, together with the N atom, are a piperidine or morpholine ring, $R^{10}$ is $C_1$–$C_4$-alkyl, $C_2$–$C_3$-alkenyl, chloromethyl, phenyl, benzyl or a group of the formula

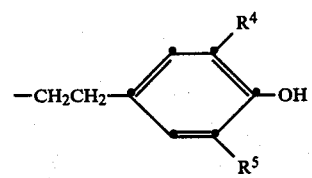

$R^{11}$ is hydrogen, methyl or phenyl, $R^{12}$ is hydrogen, $C_1$–$C_8$-alkyl, —CO—R$^{10}$ or —CO—N(R$^8$)(R$^9$), $R^{13}$ is $C_1$–$C_4$-alkyl, phenyl or p-tolyl, and A is hydrogen, $C_1$–$C_8$-alkyl, cyano, allyl or benzyl.

3. A recording material for colour photography according to claim 2, wherein the stabiliser is a compound of the formula II in which $R^2$ is hydroxyl, methyl, allyl, benzyl, 2-hydroxyethyl, acetyl, acrylolyl, methoxy, acetoxy or a —CO— N(R$^8$)(R$^9$) group, $R^4$ is tert.-butyl, $R^5$ is methyl or tert.-butyl, $R^6$ is hydrogen or $C_1$–$C_8$-alkyl, $R^8$ is $C_1$–$C_8$-alkyl, phenyl or cyclohexyl, $R^9$ is hydrogen or $C_1$–$C_8$ alkyl, and A is hydrogen, $C_1$–$C_8$-alkyl or benzyl.

4. A recording material for colour photography according to claim 1, which contains, in addition to a stabiliser of the formula I, an optical stabiliser of the ultraviolet absorber class.

5. A recording material for colour photography according to claim 1, which contains 1 to 2,000 mg of compound of the formula I per m$^2$.

* * * * *